US00PP15901P3

(12) United States Plant Patent
Bessho

(10) Patent No.: US PP15,901 P3
(45) Date of Patent: Aug. 2, 2005

(54) ***CALIBRACHOA* PLANT NAMED 'KAKEGAWA S45'**

(50) Latin Name: ***Calibrachoa* species**
Varietal Denomination: Kakegawa S45

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 288 days.

(21) Appl. No.: 10/402,387

(22) Filed: Mar. 28, 2003

(65) Prior Publication Data

US 2004/0194173 P1 Sep. 30, 2004

(51) Int. Cl.[7] ..... A01H 5/00
(52) U.S. Cl. ..... Plt./263
(58) Field of Search ..... Plt./263, 356

*Primary Examiner*—Kent Bell
(74) *Attorney, Agent, or Firm*—Jondle & Associates P.C.

(57) ABSTRACT

'Kakegawa S45' is a new variety of *Calibrachoa* plant. This new variety has deep blue colored flowers and dark green foliage.

1 Drawing Sheet

Genus/species: *Calibrachoa* species.
Varietal denomination: 'Kakegawa S45'.

BACKGROUND OF THE INVENTION

'Kakegawa S45' originated from a hybridization made in November 1998 in Kakegawa, Japan. The female parent was a *Calibrachoa* breeding line with rose colored flowers known as KL1 (not patented). The male parent was *Calibrachoa* variety 'Liricashower Blue', (U.S. Plant Pat. No. 9,885).

In August 1998, $F_1$ seed was sown from this cross and 30 plants were transplanted to outdoors. Three plants were selected for creeping and branching habit and intercrossed to produce $F_2$ seed. In February 1999 the second generation seed was planted in the field at Kakegawa and plants with different shades of blue and red flowers were observed. Two plants were selected for deep blue flower color and creeping, branching plant habit. In August 1999 these plant lines were then vegetatively propagated and grown to flowering stage in pots. Trait stability was evaluated during the summer of 2000 in greenhouses in Japan.

The breeder selected one line, for its flower color and abundance, to be vegetatively propagated and further evaluated in Salinas, Calif. during 2001. This selection was subsequently named 'Kakegawa S45' and was determined to have its trait characteristics firmly fixed. 'Kakegawa S45' was asexually reproduced by stem cuttings in Salinas, Calif. and reproduces true to type through successive generations of asexual propagation. 'Kakegawa S45' is distinguished from its parental cultivars primarily in flower color.

DESCRIPTION OF PHOTOGRAPH

This new *Calibrachoa* plant is illustrated by the accompanying photographs which show blooms, and foliage of the plant in full color, the colors shown being as true as can be reasonably obtained by conventional photographic procedures.

DESCRIPTION OF THE GENUS *CALIBRACHOA* LLAVE & LEX

Figure 1:
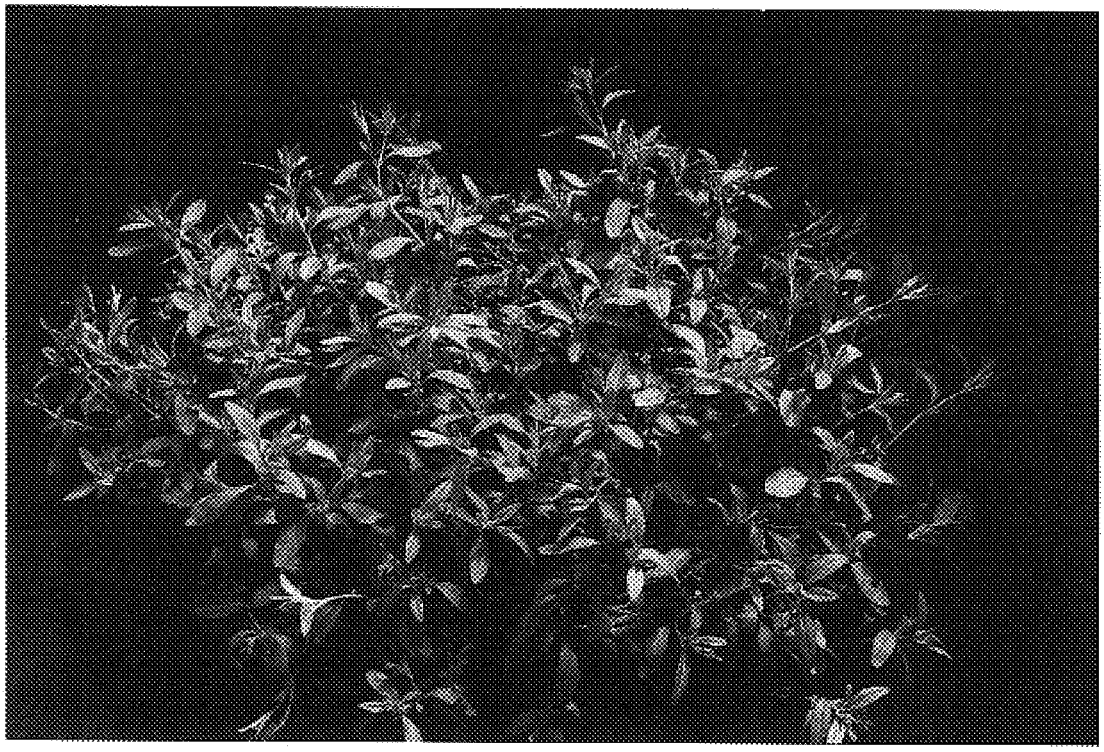
FIG. 1 shows the entire plant.
Figure 2:
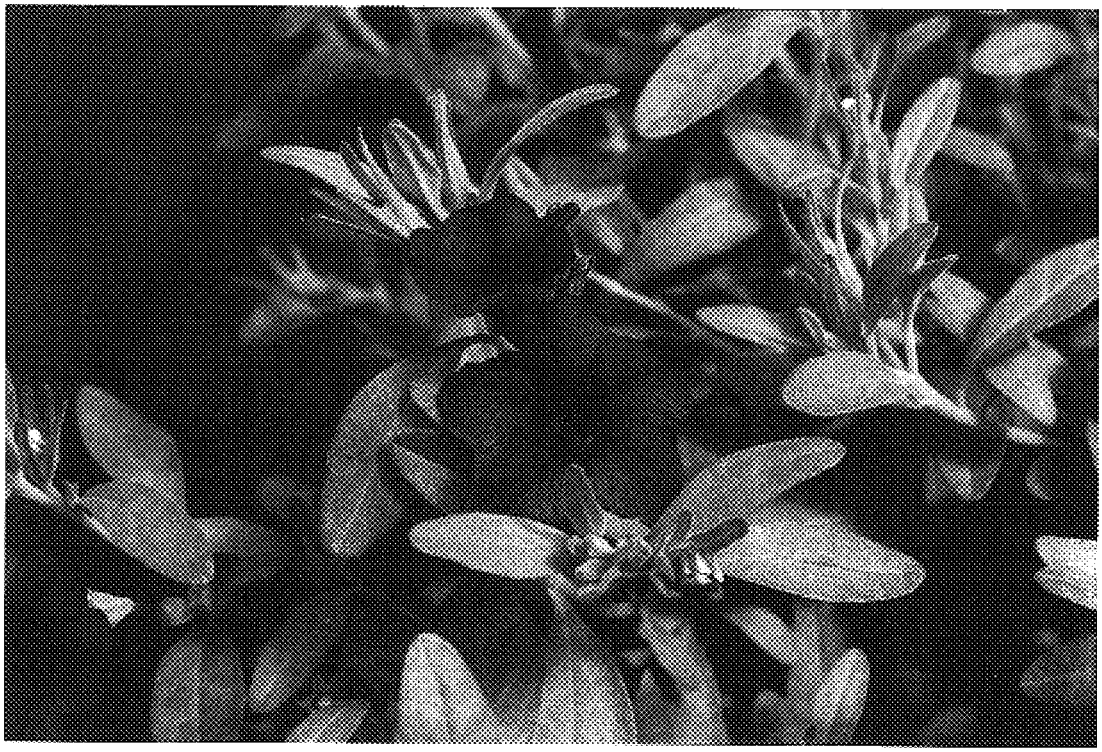
FIG. 2 shows an up close view of leaves and stems.

The genus *Petunia* was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden *Petunia,* and the inter-relationship of several species classified as *Petunia.* These studies discovered that *P. hybrida* and its ancestrial species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne.* Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, a single outermost petal covers the other four, radially folded and terminally contorted petals. *Calibrachoa* flower buds are flat with all five petals linearly folded and the two lower petals forming a cover around the three other petals and fused together.

In U.S. Plant Pat. No. 9,885, the Genus for 'Liricashower Blue' was identified as *Petunia.* Since that time, as discussed above, the inventor has learned that the Genus *Petunia* has been split by the I. N. G., and this particular variety, because of its chromosome number and bud aestivation is more accurately characterized as a member of the *Calibrachoa* Genus.

ENVIRONMENTAL CONDITIONS FOR PLANT GROWTH

The terminal 1.0 to 1.5 inches of an actively growing stem was excised. The base of the cuttings were dipped for 1 to 2 seconds in a 1:9 solution of DIP 'N GROW (1 DIP 'N GROW: 9 water) root inducing solution immediately prior to sticking into the cells trays. Cuttings were stuck into plastic cell trays having 98 cells, and containing a moistened peat moss-based growing medium. The cuttings were misted with water from overhead for 10 seconds every 30 minutes until sufficient roots were formed. The vegetative cuttings were propagated in five to six weeks.

Rooted cuttings were transplanted and grown in 20 cm diameter plastic pots in a glass greenhouse. Pots contained a peat moss-based growing medium. Soluble fertilizer containing 20% nitrogen, 10% phosphorus and 20% potassium was applied once a day or every other day. Fertilizer was applied in irrigation water. Pots were top-dressed with a slow release fertilizer containing 20% nitrogen, 10% phosphorus and 18% potassium. The typical average air temperature was 24C.

DETAILED DESCRIPTION OF THE NEW PLANT

Data below collected on plants four months from rooted cutting and transplanted into 20.0 cm diameter pots. Color references are to the R.H.S. Colour Chart of The Royal Horticultural Society of London (R.H.S.). The following traits and characteristics describe the new variety.

Classification:
- *Family.*—Solanaceae.
- *Species.*—*Calibrachoa* sp.
- *Common names.*—*Calibrachoa.*

Parentage:
- *Female parent.*—Breeding line KL1 (not patented).
- *Male parent.*—'Liricashower Blue' U.S. Plant. Pat. No. 9,885.

Growth:
- *Habit.*—Decumbent.
- *Height.*—23.0 cm.
- *Spread.*—115.0 cm when grown in a 41 cm hanging basket or pot, and using five 20 cm potted plants in one hanging basket.
- *Life cycle.*—Tender perennial.
- *Time to produce a rooted cutting.*—6 weeks.
- *Time to bloom from propagation.*—10 weeks.
- *Flowering season.*—Spring and summer.
- *Flowering requirements.*—No particular requirements, day neutral.
- *Resistance/susceptibility.*—Excellent resistance to rain, heat and drought. Will not tolerate temperatures below 10C. Plants are susceptible to *Botrytis,* powdery mildew, various stem and root rots, and certain viruses, like Tobacco Mosaic Virus and Impatiens Necrotic Spotted Virus. Plants can be infested with aphids, leafminer, whitefly and various *Lepitopdera.*
- *Form.*—Branching, dense.

Stems:
- *Stem color.*—R.H.S. 144B (yellow-green).
- *Pubescence.*—Heavy.
- *Pubescence color.*—Whitish.
- *Pubescence shape.*—Pointed.
- *Stem description.*—Round, slightly ancipital.
- *Stem length.*—3.8 cm–4.0 cm.
- *Stem diameter.*—2.0 mm.
- *Internode length.*—1.5 to 2.5 cm.

Leaves:
- *Leaf tip.*—Mucronate.
- *Leaf arrangement.*—Alternate.
- *Leaf base.*—Decurrent.
- *Leaf color.*—Upper surface: R.H.S. 137A (green); lower surface: R.H.S. 138B (green).
- *Leaf fragrance.*—Absent.
- *Leaf margin.*—Entire.
- *Leaf surface.*—Rough.
- *Leaf surface pubescence.*—Slight.
- *Petiole color.*—R.H.S. 138B (green).
- *Petiole length.*—3.0 mm.
- *Leaf length.*—3.0–3.5 cm.
- *Leaf shape.*—Elliptical.
- *Leaf width.*—8.0 mm–1.0 cm.

Flowers:
- *Calyx.*—5 sepals; 3.0×2.0 mm (l×w); free.
- *Sepal shape.*—Lanceolate.
- *Sepal apex.*—Mucronate.
- *Sepal margin.*—Entire.
- *Sepal color.*—Upper surface: R.H.S. 141B (green); lower surface: R.H.S. 141B (green).
- *Corolla.*—5 petals, fused.
- *Flower diameter.*—1.5 cm.
- *Flower depth.*—2.0 cm–2.5 cm.
- *Floral tube length.*—1.0 cm–1.5 cm.
- *Floral tube diameter.*—0.4 cm–0.5 cm.
- *Bud length.*—2 cm.
- *Bud diameter.*—0.4 cm–0.5 cm.
- *Bud color.*—R.H.S. 144D (yellow-green).
- *Bud shape.*—Ovate.
- *Bud surface.*—Pubescent.
- *Ovary.*—Superior.
- *Duration of flower life.*—5 days.
- *Flowering habit.*—Indeterminate.
- *Pistil number.*—1.
- *Peduncle size.*—1.0 mm diameter; 2.5 mm length, slightly, short pubescence.
- *Peduncle color.*—R.H.S. 144B (yellow-green).
- *Inflorescence type.*—Solitary.
- *Stamens.*—Free.
- *Stamen color.*—R.H.S. 7C (yellow).
- *Stigma color.*—R.H.S. 149A (yellow-green).
- *Style color.*—R.H.S. 149A (yellow-green).
- *Petal size.*—2 mm×1 mm (l×w).
- *Petal shape.*—Spatulate.
- *Petal apex.*—Truncate.
- *Petal margin.*—Entire.
- *Petal color.*—Upper surface: R.H.S. 83B (violet) with R.H.S. 86A (violet) mid-vein and corolla throat; lower surface: R.H.S. 79C (purple); corolla tube:

inner surface: R.H.S. 3C (yellow) with R.H.S. 86A (violet) veins; outer surface: R.H.S. 9C (yellow) with R.H.S. 79C (violet) veins.

*Pollen color.*—R.H.S. 9B (yellow).

*Produces seed.*—None.

COMPARISON WITH MOST SIMILAR VARIETY

'Kakegawa S45' is a distinct variety of *Calibrachoa* owing to its deep blue flower with dark purple throat and a yellow tube. 'Kakegawa S45' is most similar to the variety 'Sunbelkubu' (U.S. Plant Pat. No. 10,279) however there are numerous differences as shown in the table below.

TABLE 1

| Characteristic | 'Kakegawa S45' | 'Sunbelkubu' |
|---|---|---|
| Stem and Leaf Pubescence | Heavy | Slight |
| Upper Petal Mid-vein | Distinct color from petal surface | Same color as petal surface |
| Pollen Color | RHS 9B (yellow) | RHS 5B (yellow) |

What is claimed is:

1. A new and distinct *Calibrachoa* plant as shown and described herein.

* * * * *